(12) United States Patent
Bockel-Macal et al.

(10) Patent No.: US 6,788,998 B2
(45) Date of Patent: Sep. 7, 2004

(54) PROCEDURE AND APPARATUS FOR THE OPTIMIZATION OF REACTIVE GAS MIXTURES

(75) Inventors: Savine Bockel-Macal, Paris Cedex (FR); Fabien Illy, Paris Cedex (FR); Pierre Avrillier, Paris Cedex (FR)

(73) Assignee: L'Air Liquide Societe Anonyme a Directoire et Conseil de Surveillance pour l'Etude et l'Exploitation des Procedes Georges Claude, Paris (FR)

( * ) Notice: Subject to any disclaimer, the term of this patent is extended or adjusted under 35 U.S.C. 154(b) by 420 days.

(21) Appl. No.: 09/759,265

(22) Filed: Jan. 16, 2001

(65) Prior Publication Data

US 2001/0009773 A1 Jul. 26, 2001

(30) Foreign Application Priority Data

Jan. 25, 2000 (FR) ............................................. 00 00946

(51) Int. Cl.$^7$ .......................... G01N 33/22; G05B 21/00
(52) U.S. Cl. ........................... 700/266; 422/62; 436/143
(58) Field of Search .......................... 700/266; 422/62; 346/143; 436/143

(56) References Cited

U.S. PATENT DOCUMENTS

| | | | |
|---|---|---|---|
| 4,852,384 A | * | 8/1989 | Woolbert et al. ............ 73/1 G |
| 5,882,618 A | | 3/1999 | Bhatia et al. |

FOREIGN PATENT DOCUMENTS

| | | |
|---|---|---|
| EP | 0 761 299 | 3/1997 |
| EP | 0 854 204 | 7/1998 |
| FR | 2 713 105 | 6/1995 |

OTHER PUBLICATIONS

Hempseed, J. W. Chemical Abstracts 1988, 108, abstract 81199v.*

Yoshikawa, H. et al, Chemical Abstracts 1993, 119, abstract 187558d.*

Soundarajan, R. et al, Chemical Abstracts 1994, 120, abstract 222148q.*

O'Shaughnessey, D. Chemical Abstracts 1995, 122, abstract 317838v.*

Clark, D. G> et al, Chemical Engineering Progress 1996, 92, 65–77.*

Guedes F. et al, Mineracao Metalurgia 1986, 50, 56–58.*

Yoshikawa, H. et al, Koatsu Gasu 1993, 30, 273–285.*

Kaderabek, V. Proceedings of the International Pyrotechnics Seminar 1994,□□20TH, 515–532.*

O'Shaughnessey, D. et al, Process Safety Progress 1995, 14, 22–25.*

Hoyle, M. et al, Institution of Chemical Engineers Symposium Series 1997,□□141, 293–304.*

Mashuga, C. V. et al, Process Safety Progress 1998, 17, 176–183.*

Nair, M. P. S. CEW, Chemical Engineering World 1998, 33, 87–92.*

\* cited by examiner

*Primary Examiner*—Arlen Soderquist
(74) *Attorney, Agent, or Firm*—Burns, Doane, Swecker & Mathis, L.L.P.

(57) ABSTRACT

The invention relates to a procedure for determining the risk of flammability of a mixture of two reactive gases A, B, in an inert or base gas, which includes: a step of determining, in the flammability diagram for the A/B/base gas mixture, the change in the composition of the mixture in order to determine whether or not the composition has passed through the flammability region of the flammability diagram, when A is firstly injected into the inert or base gas to form a first mixture and then B is injected into the first mixture in order to form the final mixture; a step of comparing the mixing time, should the region have been passed through, with the chemical induction time for the mixture.

20 Claims, 9 Drawing Sheets

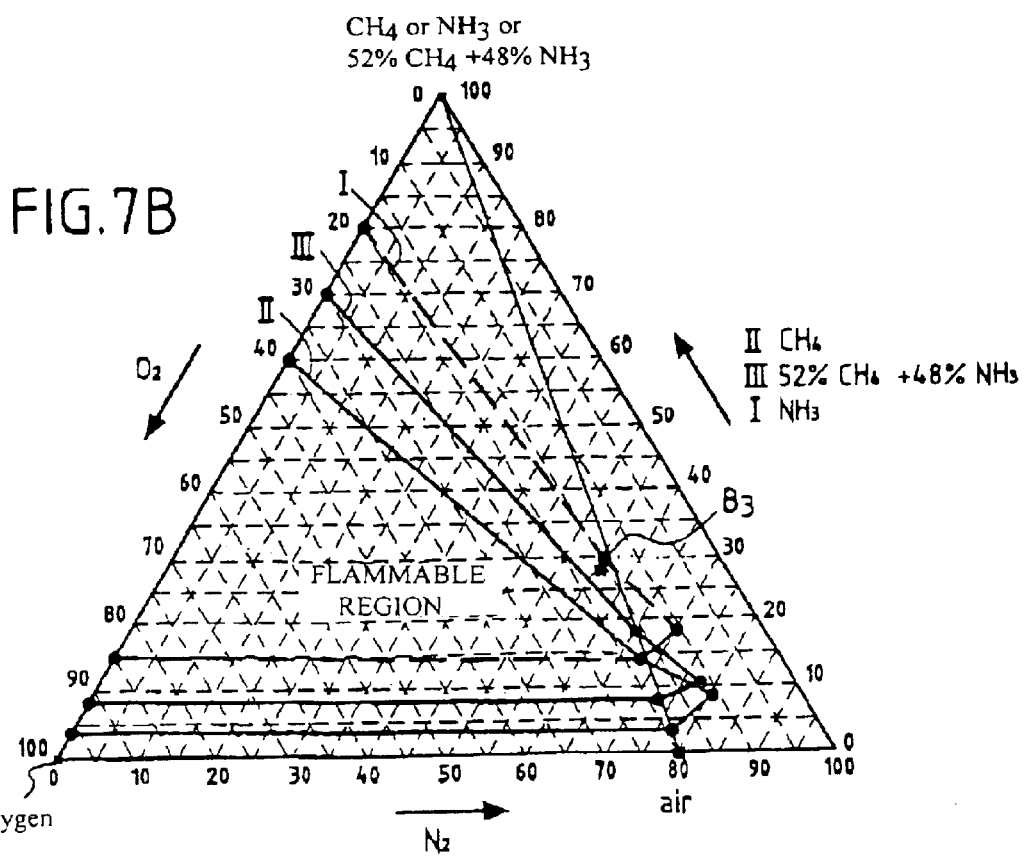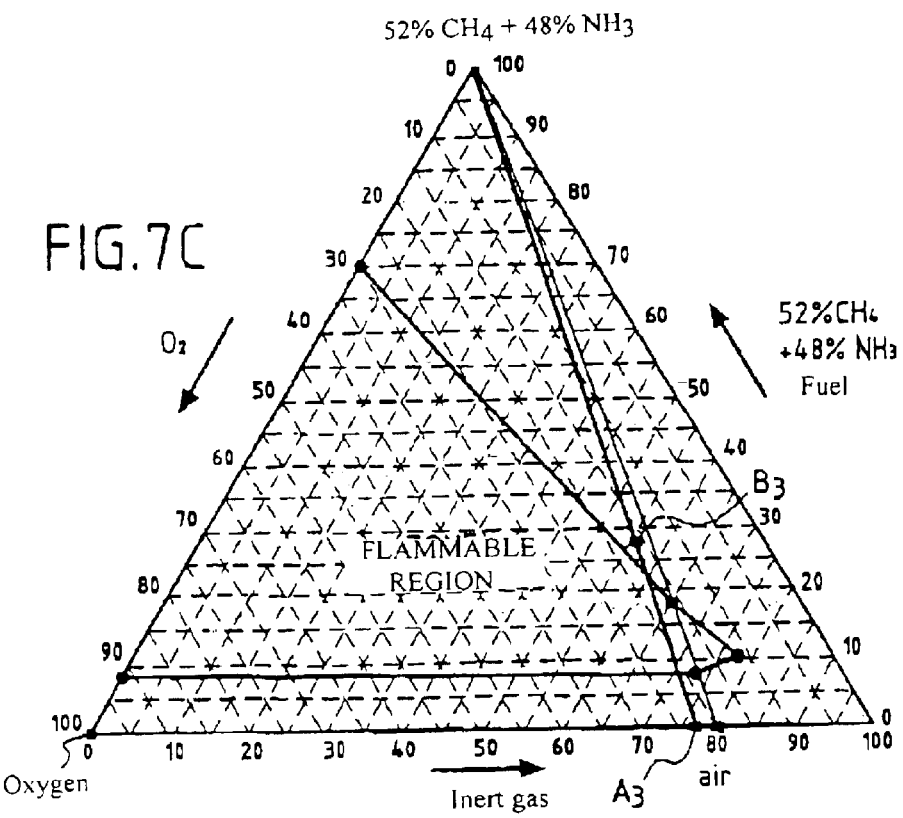

PROCEDURE AND APPARATUS FOR THE OPTIMIZATION OF REACTIVE GAS MIXTURES

BACKGROUND OF THE INVENTION

1. Field of the Invention

The invention relates to the production of potentially reactive gas mixtures and to the determination of schemes for mixing such gases.

2. Description of the Related Art

In order to reduce potentially reactive gas mixtures completely safely, various mixing methods and/or apparatuses have been proposed at the present time, which methods take into account the capability of the static mixture; that is to say only the quality of the final mixture is considered.

This is the case, for example, with document U.S. Pat. No. 5,801,265 which relates to a method of injecting oxygen into a reactant, for which a control device ensures that an oxygen/reactants mixture has a final composition lying above a certain upper flammability limit.

Studies on gas mixtures in burners generally concern the reaction of the gases and in particular the combustion products which must satisfy a precise specification (particularly, low NOx formation and limitation in the maximum temperature).

At the present time, there is no method making it possible to determine a gas injection scheme which takes into account the change in the composition of the mixture while it is being produced.

SUMMARY OF THE INVENTION

The invention provides another approach so as to determine the possibilities of producing a potentially flammable gas mixture.

More specifically, the invention provides a study of the use of a mixture of reactive gases, taking into account the actual mixing phenomenon, i.e. the risks owing to the reactivity which may arise during the mixing phase.

The invention relates especially to a procedure for determining the risk of flammability of a mixture of at least two reactive gases A, B, in an inert gas or a base gas (a gas possibly containing the gases A, B and other species, which may or may not be reactive) or for determining the order of mixing of the reactive gases in the inert or base gas.

The term "inert gas" should particularly be understood to mean a gas that does not lead, under the mixing conditions, to chemical reactions with A or B or with itself.

Modes of mixture formation (or mixing modes) are defined, according to the order in which the reactive gases are successively mixed into the inert or base gas: according to a first mode, the gas A is firstly mixed into an inert or base gas, forming with the latter a first mixture into which the gas B is then mixed; according to a second mode, the gas B is firstly mixed into the inert or base gas, forming with the latter a first mixture into which the gas A is then mixed. If the mixture involves more than two gases in the inert or base gas, further modes of mixture formation may be defined.

Starting from the ternary diagram for the mixture in question (whether this is a mixture of two or more gases in the inert gas or base gas), it is possible to determine the change in the composition of the mixture when A is firstly injected into the inert gas, or the base gas, in order to form a first mixture and then B is injected into the first mixture in order to form the final mixture.

Examination of the ternary diagram provides direct information about the composition of the mixture with respect to its flammability region, something which is not the case if binary diagrams are used.

If the composition of the mixture changes within the ternary diagram without entering the flammability region, this mode of injection may be adopted since its flammability risk is zero.

It is also possible to compare, for one or both mixing modes, the transit time spent by the mixture, during its formation, passing through the flammability region of this diagram, or the mixing time (which is greater than the transit time), with the chemical induction time for this same mixture.

The mixing time is linked with the technology of the mixer. This is because it depends on the velocities of the flow generated by the mixer and on its ability to mix rapidly.

The subject of the invention is therefore a procedure for determining the risk of flammability of a mixture of at least two reactive gases A, B, in an inert or base gas, or the order of mixing of these reactive gases into the inert or base gas, characterized in that it comprises:

- a step for determining whether the composition of the mixture, during its formation, passes through the flammability region in the ternary diagram of the A/B/base (or inert) gas mixture when this mixture is produced according to a first mode in which A is firstly mixed into the inert or base gas in order to form a first mixture and then B is mixed into the first mixture in order to form the final mixture.

This procedure may furthermore include:

- a step of determining a first transit time through the flammability region of the said ternary diagram, this transit time depending on the mixture used during the phase of producing the mixture which forces the composition to pass through the flammability region;
- a step of comparing this first transit time with the chemical induction time of the mixture; the latter time depends of the reactivity of the mixture.

According to a variant, it is the mixing time, characteristic of the mixer used during the phase of producing the mixture which forces the composition to pass through the flammability region, which is compared with the chemical induction time of the mixture.

If the composition of the mixture passes through the flammability region of the said ternary diagram, or else if the mixing time involved or the first transit time is greater than the chemical induction time of the mixture, the following steps may also be carried out:

- a step for determining whether the composition of the mixture, during its formation, passes through the flammability region in the ternary diagram of the A/B/base (or inert) gas mixture, when the latter is produced according to a second mode in which B is firstly mixed into the inert or base gas in order to form a first mixture and then A is mixed into the first mixture in order to form the final mixture, and, optionally:
- a step of comparing the mixing time of the mixer, used during the phase of producing the mixture which forces the composition to pass through the flammability region, with the chemical induction time of the mixture when B is firstly mixed into the inert or base gas in order to form a first mixture and then A is mixed into the first mixture in order to form the final mixture; or else
- the determination of a second transit time within the flammability region of the said ternary diagram when B is firstly injected into the inert or base gas in order to form a first mixture and then A is injected into the first mixture in order to form the final mixture, and a step of comparing this second transit time with the chemical induction time of the mixture.

Preferably, it is the minimum chemical induction time which is compared with the mixing time. The induction time for the stoichiometric mixture is generally close to this minimum induction time and may be taken as an approximation of this minimum time.

The procedure according to the invention therefore takes the mixing phenomenon into account. It makes it possible, based on the flammability characteristics of the gas mixture composed of A, B and the inert or base gas, and on the characteristics of the mixers used, to evaluate the flammability risk while A is being mixed into B, the latter already being mixed with the inert or base gas, or while B is being mixed into A, the latter already being mixed with the inert or base gas, more than simply knowing whether or not the final A+B+inert or base gas mixture would be flammable.

The invention also makes it possible to evaluate the most judicious and safest solution in order to know which fluid to mix first and foremost and to know how to produce the mixture. This is especially the case when the invention is applied to injections of two reactive fluids into a predominantly inert stream, as in recycling processes.

The procedure according to the invention may apply to a mixture of several gases, the number of gases to be mixed being greater than three.

One procedure for mixing two reactive gases A, B into an inert or base gas therefore comprises:

determining the flammability risk of the mixture, while the mixture is being produced, or determining the order of injection of the reactive gases, using the procedure according to the invention and described above;

mixing the reactive gases A and B in the order for which the composition of the mixture does not pass through the flammability region while the composition is changing, or for which the mixing time(s) or the transit time through the flammability region of the ternary diagram is (are) less than the chemical induction time of the mixture.

According to the invention, the case in which at least three reactive or fuel gases are mixed with an inert or base gas may amount to the successive treatment of several cases of mixing two gases with an inert or base gas.

Implementation of the invention may be helped by consulting electronic databases.

The invention also relates to a procedure for producing a plant for mixing at least two reactive gases A, B into an inert or base gas, comprising the following steps:

the order of mixing these gases is determined using a procedure as described above;

a plant is produced so as to mix the gases in the order thus determined.

Thus, mixers may be placed in a line supplying the inert or base gas, so that the mixing of the gases takes place under very safe conditions.

The invention therefore makes it possible to produce, with a high degree of safety, a plant for mixing at least two reactive gases A, B into an inert or base gas.

The subject of the invention is also an apparatus for implementing the invention, characterized in that it comprises:

means for storing at least one database containing, for gas mixtures, data on the ternary diagrams of these mixtures, and the flammability regions in these diagrams for given temperature and pressure conditions;

means for selecting a gas mixture and pressure and temperature conditions to be used for this gas mixture;

means for displaying a ternary diagram and the flammability region of a mixture in this diagram.

According to another aspect, the subject of the invention is also an apparatus for establishing the flammability risk of mixtures, each mixture consisting of at least two reactive gases A, B in an inert or base gas, or for establishing the order of mixing of these reactive gases into the inert or base gas, characterized in that it includes means for computing, or means especially programmed for computing, as a function of temperature and pressure conditions:

the ternary diagram of a mixture and the flammability region in this diagram;

a chemical induction time of these mixtures. The latter parameter depends on the temperature, pressure and concentration.

Finally, the subject of the invention is a terminal for establishing the flammability risk of a mixture of at least two reactive gases A, B in an inert or base gas, or the order of mixing these reactive gases into the inert or base gas, characterized in that it comprises:

communication means for communicating between the said terminal and means containing at least one database which includes, for gas mixtures, data on the ternary diagrams of these mixtures, and the flammability regions in these diagrams as a function of the temperature and pressure conditions;

means for supplying the said terminal with data for the user of the said terminal, including at least one gas mixture used, and the temperature and pressure conditions of use, and optionally one or more types of defined mixers;

storage means, communicating with the means for supplying the said terminal with the user data, in order to store this user data, as well as data supplied by the database on the ternary diagram of the mixture selected;

display means, communicating with the storage means, in order to display at least the ternary diagram supplied by the database, and optionally the mixing time for a defined mixer.

The invention makes it possible, by consulting databases, to construct a set of information describing the behaviour of a gas mixture.

Thus, the arrangement of a plant intended for mixing gases may be quickly established, thereby shortening the design time for this plant.

BRIEF DESCRIPTION OF THE FIGURES

The characteristics and advantages of the invention will become more apparent in the light of the description which follows. This description relates to illustrative examples, given by way of explanation but implying no limitation, with reference to the appended drawings in which:

FIGS. 7B and 7C show flammability diagrams of fuel/oxidizer/inert gas mixtures;

DETAILED DESCRIPTION OF EMBODIMENTS OF THE INVENTION

Figure 1:
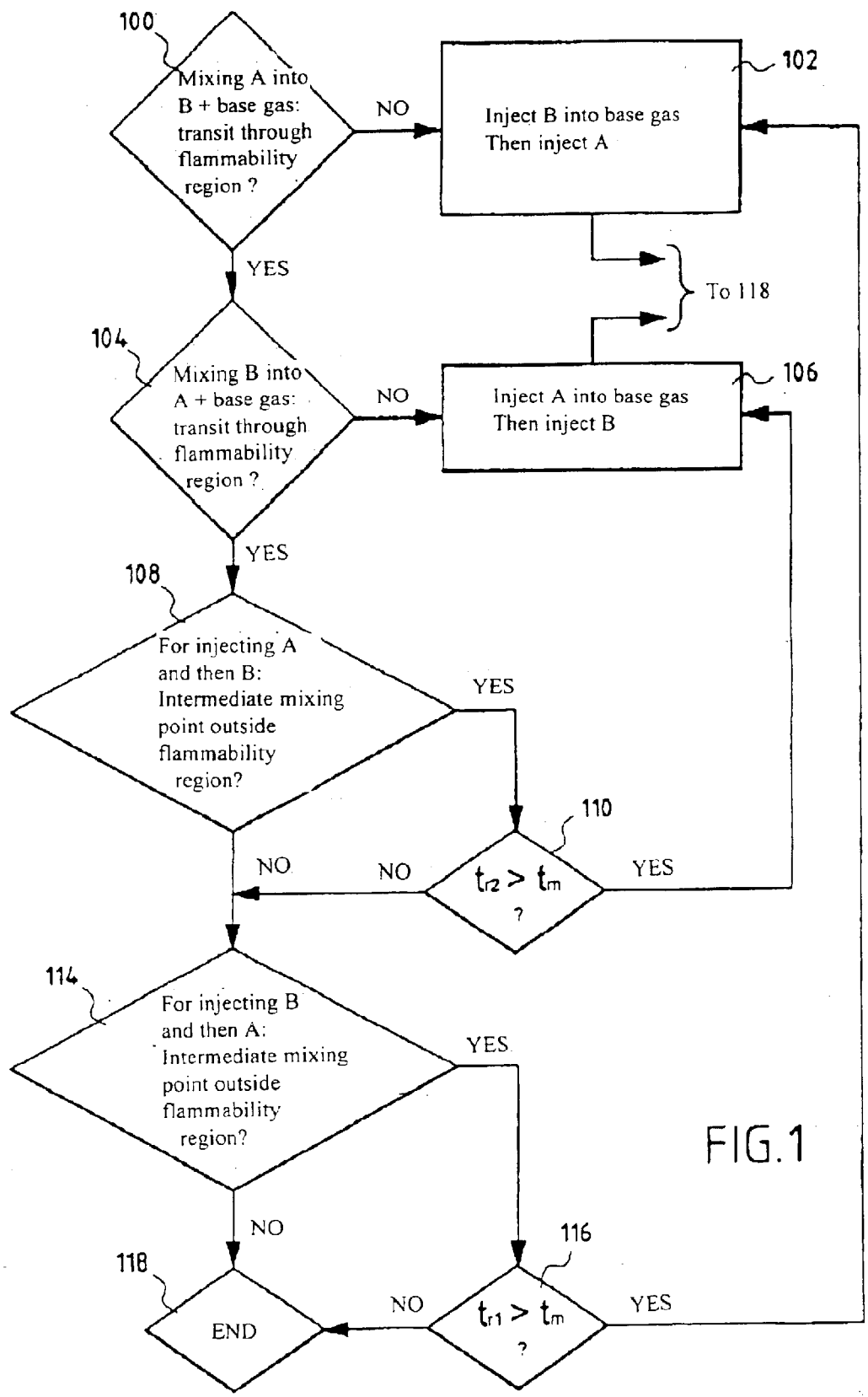
FIG. 1 shows a flow diagram of a procedure according to the invention.

Steps in procedures according to the invention will be explained in conjunction with FIG. 1.

This figure relates to the case of mixing two gases A and B into a base gas, for example an inert gas.

According to the invention, it has already been determined (step 100) whether, when mixing A into B (B already having been mixed with an inert gas), the latter is flammable.

In other words, it has been determined whether the composition of the A/B/base gas ternary mixture passes through the flammability region of the flammability diagram (ternary diagram), during formation of the mixture, when:

firstly B is mixed into the base gas using a first mixer, in order to form a first mixture;

then, using a second mixer, A is mixed into the first mixture obtained, in order to form the final mixture.

This flammability region in the ternary diagram may, for example, be determined using Le Chatelier's law, which allows the flammability regions to be plotted using mixtures of fuels. Reference may be made on this subject to Kuchta, Bulletin 680, Bureau of Mines, 1985.

If the composition does not pass through the flammability region, the following order of injection may be adopted as the order to be employed(step 102):

B is firstly mixed into the base gas (first mixture)

A is then mixed into the first mixture.

This is because the flammability risk for this order of mixing is zero.

However, if this first mixing mode means that the composition passes through the flammability region, the other possibility of forming the mixture (second mode) is considered (step 104), namely:

mixing A into the base gas (first mixture) using a first mixer;

then, using a second mixer, mixing B into the first mixture.

If this second mode of mixing the gases A and B does not force the composition to pass through the flammability region (step 104), then this second mode is adopted (step 106), the flammability risk being zero.

If both modes thus defined both force the composition to pass through the flammability region, there is then a flammability risk. However, this risk is under control if the order of mixing adopted is that which satisfies the following two criteria:

(i) the intermediate mixture (first mixture) point lies outside the flammability region; this first criterion aims to exclude the case in which the intermediate mixture formed would itself exhibit flammability characteristics, a situation which would be very dangerous and which would have a very high flammability risk;

(ii) the mixing time in the mixer used during the phase or step which forces the composition to pass through the flammability region is less than the chemical induction time or spontaneous ignition time of the mixture. This second criterion is in fact a comparison between the reactivity of the mixture and the performance (mixing time) of the mixer.

The reactivity of the mixture is characterized by an induction time or ignition time: both before the steady state has been established and before the actual explosion, a certain time elapses, this being called the induction period or spontaneous ignition time, depending on whether it precedes a slow ramification or an explosive reaction. The length of these initial periods varies according to the nature of the reactants involved.

More specifically, when a flammable mixture is brought to a temperature and pressure such that it can explode, the spontaneous ignition occurs only after a certain time: this time is denoted by the term "spontaneous ignition time". The order of magnitude of this time varies according to the initial temperature and pressure levels. It also depends on the concentrations of the components of the mixture.

For example, the spontaneous ignition time of heptane in air in stoichiometric proportions at 12 bar goes from 10 seconds (at 400° C.) to 25 ms (at 500° C.). In the case of stoichiometric hydrogen in air at atmospheric pressure, the spontaneous ignition time goes from 100 ms (at 560° C.) to 15 ms (at 630° C.). (Reference may be made to the work by A. Van Tiggelen "Oxydations et Combustions [*Oxidations and Combustions*]", volume 1, Publications of the French Institute of Petroleum, 1968, published by Technip). The gas stream method, or flow method, also called concentric tube method, allows spontaneous ignition times longer than 0.5 ms to be measured experimentally. Reference may be made, concerning this method, to the abovementioned work by Van Tiggelen. The fuel, diluted or undiluted, and heated to the desired temperature, flows along a thermostatted pipe. At a given section, a fuel, generally preheated, is injected.

According to another method of determination, the equations governing the kinetics of the fuel reactions involved are set up and these are solved numerically.

As regards the mixing time, this is intrinsic to the technology of the mixer. It is determined by knowing parameters such as the mean travel time or the particulate travel time in the mixture.

The mixing time is the time that elapses before a certain homogeneity of the mixture is reached. This homogeneity may, for example, be represented by the variation coefficient, defined by the ratio of the standard deviation of the concentration distribution to the mean of this distribution, for example when the concentration distribution is weighted by the mass flow rate. A mixture is regarded as being mixed when the variation coefficient is less than 1% or less than 2% or less than 5%.

The overall mixing time may be determined experimentally by concentration measurements (probe measurements, tomography, laser-induced fluorescence) and velocity measurements (laser Doppler velocimetry and particle image velocimetry).

An injector is an example of a mixer.

Typically, the overall mixing times corresponding to the injector described in U.S. Pat. No. 5,356,213 vary from 100 to 500 ms.

Knowing in detail the velocity and concentration fields allows particulate mixing times to be obtained using numerical tools (fluid mechanics code for solving the Navier-Stokes equations).

The work entitled "Measurement Techniques in Fluid Dynamics", Von Karman Institute for Fluid Dynamics, 1994, V.K.I. Library, ISBN: D/1994/0238/417, gives additional information about the techniques for determining the abovementioned mixing times.

The mixing time, for an initial state and a final state which lie outside the flammability region of the ternary diagram is greater than the transit time spent by this mixture in this region.

Consequently, according to FIG. 1, it is determined whether, if the answers to the questions asked at steps 100 and 104 are in the affirmative, the intermediate mixture point in the case of the second injection mode lies outside the flammability region (step 108). If yes, the reactivity time $t_{r2}$ of the mixture for this second mode is compared with the time $t_m$, or mixing time, characteristic of the mixer used during the phase or step which forces a composition to pass through the flammability region (step 110). If $t_{r2} > t_m$, the flammability risk is under control and the second injection mode may be adopted as the mixing scheme to be carried out.

Otherwise, similar steps (114 and 116) are employed for the first injection mode. The reactivity time $t_{r1}$ of the mixture for this first mode is compared with the time $t_m$, or mixing time, characteristic of the mixer used during the phase or step which forces the composition to pass through the flammability region (step 116). If $t_{r1} > t_m$, the risk is under control and the first injection mode may be adopted as the mixing scheme to be carried out.

It is preferable to compare the minimum reactivity time with the mixing time.

If the final mixture is a stoichiometric mixture, then $t_{r1} \approx t_{r2}$. In other words, in this case, the reactivity time is approximately the same whatever the order in which the mixture is formed.

Moreover, the reactivity time $t_{rs}$ of the stoichiometric mixture is generally close or similar to the minimum reactivity time for the mixture in question.

If $t_m$ is compared with $t_{rs}$ and if $t_m < t_{rs}$, then the mixture can be formed in any order. In other words, the risks associated with the two approaches (firstly B in the base gas and then A, or conversely) are both under control and it is possible to choose one mixing order or the other.

If none of the injection modes satisfies the criteria imposed, the flammability risk is no longer under control and the desired mixture cannot be formed under sufficiently safe conditions. The algorithm is then terminated (step 118).

The scheme in FIG. 1 may also be modified, without departing from the scope of the invention, by carrying out successive tests on the injection modes in the reverse order. It is also possible to reverse only the order in which the two injection modes in steps 108–110 and 114–116 are considered.

According to another variant, in the second part of the diagram, that is to say after step 104, and if the answer to the question asked at this step is in the affirmative, the following procedure may be carried out:

firstly, during one and the same step, or a group of successive steps, the mode for which the intermediate point lies outside the flammable region is determined;

and then, subsequently, during one and the same step, or a group of successive steps, the reactivity of the two mixtures (A in B/inert gas and B in A/inert gas) is compared with the performance characteristic(s) of the mixture(s).

According to this variant, the mixing adopted will be the same as when the procedure is carried out according to the order contained in the diagram in FIG. 1.

According to FIG. 1, two steps allowing several modes or orders of injection to be compared with each other are employed:

first step: does the composition pass through the flammability region during mixing? An order or mode of injection of the fluids is chosen if this order or mode prevents the composition from passing through the flammability region while forming the mixture (zero flammability risk). If the formation of the mixture requires the composition to pass through the flammability region, whatever the order or mode of injection, that order or mode of injection which places the intermediate mixing point outside the flammable region is firstly considered; the second step is then carried out;

second step: comparison, for the order or mode of injection in question, between the reactivity of the mixtures and the performance characteristics of the mixers or the performance characteristic of the mixer used during the phase or step which forces the composition to pass through the flammability region, as already described above. The flammability of the mixture being formed, with or without a controlled risk, is deduced from this comparison.

According to the invention, it is therefore possible to associate with the production of the mixture and even at each step in its production, a flammability risk. This risk may be:

zero, especially if the composition does not pass through the flammability region of the ternary diagram.

or controlled, especially if the mixing time is less than the chemical induction time of the mixture;

or not controlled at all, particularly if the mixing time is greater than the chemical induction time of the mixture or if an intermediate mixture is formed whose composition lies within the flammability region of the mixture.

Attempts are in fact made to determine the mode of injection of the gases which minimizes this risk. In some cases, the risk cannot be reduced to zero or to an acceptable level. The mixing of the gases then has to be modified in order to be able to propose another mode of injecting the gases.

For each mode, a degree of risk (zero or acceptable or high risk) may be assigned according to he highest degree of risk obtained for each of its steps or equal to this highest degree of risk. For example, if the formation of a mixture according to a certain mode includes a high-risk step, the entire mode will be assigned the high risk. On the other hand, if one step has a zero risk and another step an acceptable risk, the entire mode will be regarded as being acceptable.

The ternary diagram is used to determine the change in the composition of the mixture and therefore to obtain important information about the risk associated with each step in the formation of the mixture.

A plant for which the order of injection of the gases has been able to be determined using a method as described above may then be produced.

Such a plant includes, in particular, gas supply lines and mixers (for example, injectors) placed so as to mix the gases in the order of mixing defined above.

The invention also makes it possible to carry out the mixing operations at high temperature.

The mixing times generally change from approximately 100 milliseconds to several hundreds of milliseconds, for example from 100 to 500 milliseconds in the case, already mentioned above, of the injector described in U.S. Pat. No. 5,356,213.

As regards the chemical induction times, these may change according to the nature of the fuel between a few minutes (especially under ambient temperature and pressure conditions) and values as short as a few tens of milliseconds (this being the case, in general, at high temperature, for example in the region of 500° C.–600° C.). Examples of such spontaneous ignitions times have already been given above in the case of stoichiometric heptane/air and hydrogen/air mixtures.

There therefore exists, for each given gas mixture and each given mixer, a limit temperature below which the mixing time is less than the spontaneous ignition times. This limiting temperature therefore defines a safety region above which the kinetics become very rapid, there then being risks of ignition of the mixture.

For a given mixture, knowing the change in the spontaneous ignition times or in the chemical induction time as a function of temperature, it is possible to calculate this limiting temperature at which the spontaneous ignition time becomes of the order of magnitude of, or equal to, the mixing time.

One particular illustrative example of the invention relates to a chemical process with a loop.

Figure 2A:
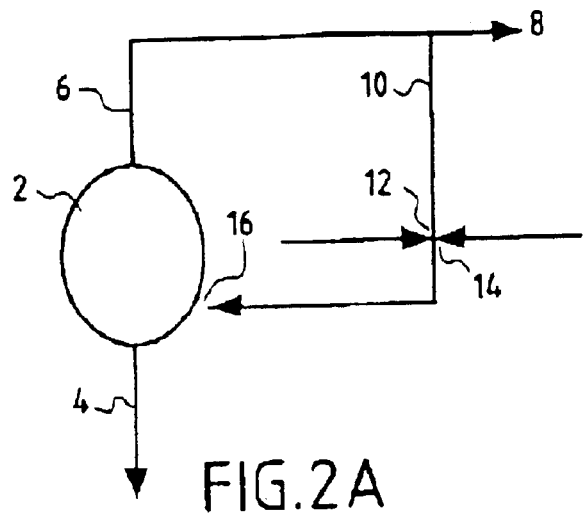
FIGS. 2A, 3A and 4A show various schemes for mixing a combustible gas and an oxidizing gas into a recycle gas.

Such a process is shown schematically in FIG. 2A. In this figure, the reference 2 denotes a reactor whose inlet 16 is fed with a mixture of a combustible gas, an oxidizer and a recycle gas.

The reactor 2 produces a product 4, as well as a gas 6 partially removed by a purge 8. This gas 6, composed of unreacted reactants, of by-products (CO) and inert gases ($N_2$, $H_2O$, etc.), therefore contains a certain proportion of fuel and of oxidizer which it is appropriate to recycle in a recycle path 10.

Over the recycle path, the oxidizer and the fuel are injected at two mixing points 12, 14, respectively. A mixer, at each of these points 12, 14, carries out this mixing. The final mixture feeds the reactor 2.

Such a recycle scheme does not separate the fuel from the oxidizer gas.

In other words, a mixture is injected at the inlet 16 of the reactor, this mixture containing oxidizer, fuel and recycle gas.

The composition of the gas injected at the inlet 16 of the reactor and the conditions under which this mixture is injected are chosen so as to reduce any risk of flammability.

Figure 2B:
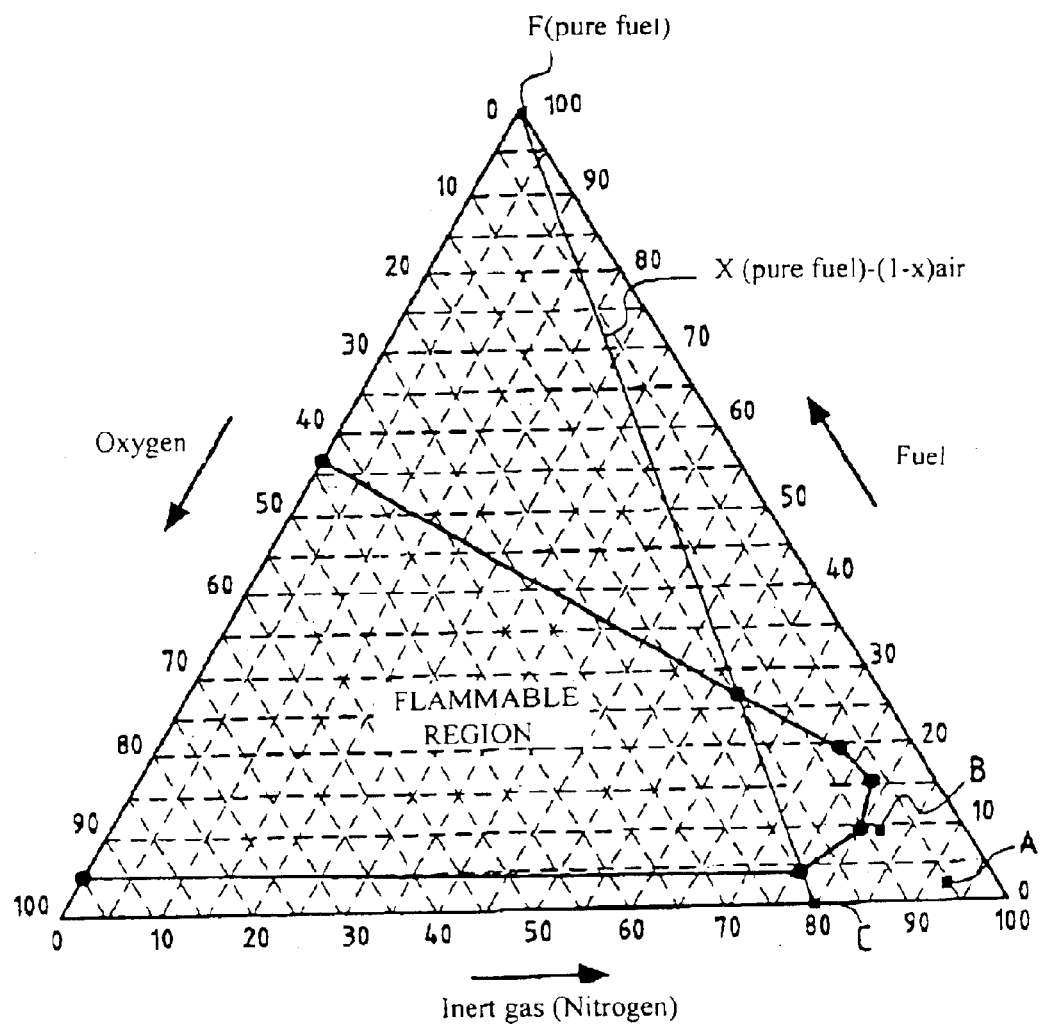
FIGS. 2B, 3B, 4B and 5A–6B represent flammability diagrams of fuel/oxidizer/inert gas mixtures.

FIG. 2B shows a fuel/oxidizer/inert (recycle) gas ternary diagram.

In this diagram, the point A corresponds to the composition of the recycle gas mixture or of the mixture leaving the reactor, before oxidizer and fuel injection. This mixture consists mostly (approximately 92% in the example given) of inert gases to which the combustible gas and the oxidizer gas are mixed in small proportions (approximately 3% in the case of the fuel and 5 to 6% in the case of the oxidizer).

The initial mixture constituting the recycle gas therefore lies outside the flammable region of the flammability diagram.

The point B represents the composition of the mixture injected into the inlet 16 of the reactor. It may be seen that this point B also lies outside the flammability region. It corresponds to an inert gas/fuel/oxidizer mixture richer in fuel and in oxidizer than the mixture represented by the point A. For example, the point B corresponds to a composition containing approximately 82% inert gas, approximately 9% fuel gas and approximately 9% oxidizer.

Consequently, in this situation, both the recycle gas coming from the reactor 2 and the mixture injected at the inlet of the reactor lie outside the flammability region and the situation could a priori be considered to be away from any danger of flammability.

The fuel-air line (F-C) in FIG. 2B represents a set of compositions for which the mixture consists of x% fuel in (1-x)% air, x changing from 0 to 1. This mixture is flammable when x changes from 0.04 to 0.26. Even if the final mixture lies outside this range, the composition, during formation of the mixture, passes through the flammability region for a certain time. The same applies for any mixture of two gases of fixed composition. Even if the two gases and the final mixture point lie outside the flammability region, the composition may pass through this region during the mixing phase and present a danger.

Figure 3A:
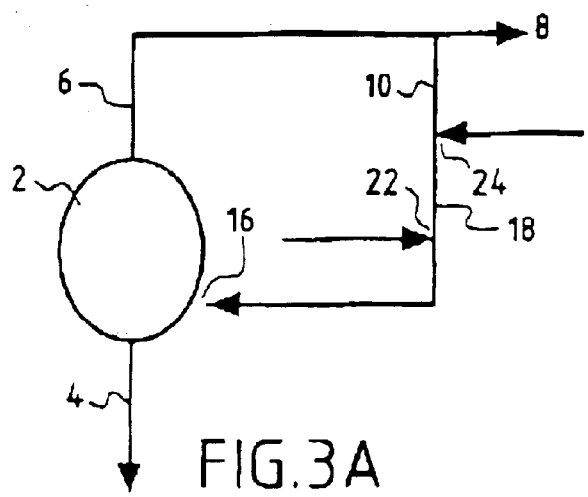

FIG. 3A shows a recycle scheme in which identical references to those in FIG. 2A denote identical or corresponding components. This scheme differs from that in FIG. 2A by the order of injection of the fuel and oxidizing gases. The fuel is firstly injected at the point 24, thereby temporarily forming a first recycle gas/fuel mixture 18. The oxidizer gas is only injected afterwards, at point 22, in order to supply the inlet 16 of the reactor with a fuel/oxidizer/recycle gas mixture.

Figure 3B:
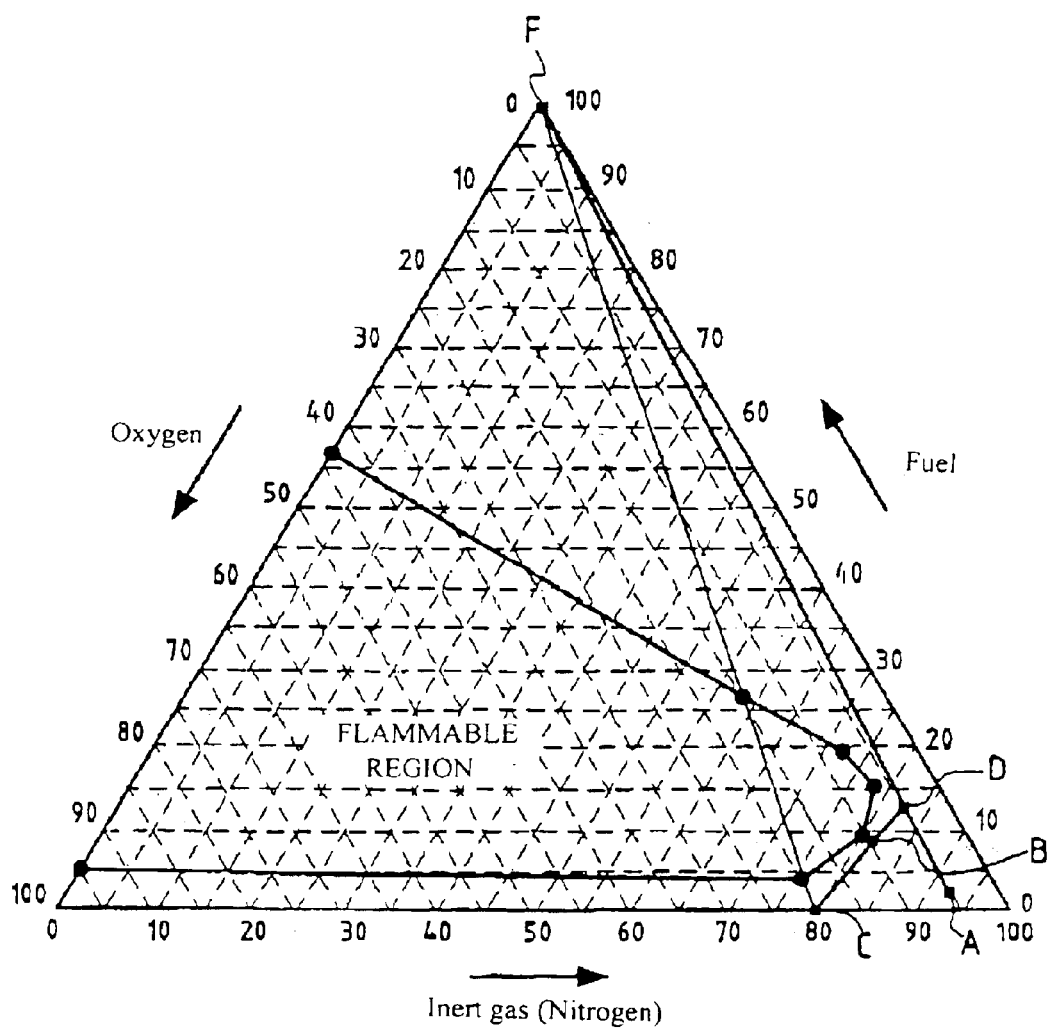

In the flammability diagram in FIG. 3B, the starting point (recycle gas composition) corresponds to the point A, as in FIG. 2B.

Likewise, the composition of the mixture entering the reactor 2 is again identified by the point B, with the same compositions as indicated above in conjunction with FIG. 2B.

The injection of pure fuel gas (the composition represented by the point F), at the point 24, causes the composition of the mixture to change from the point A to the point D, that is to say a composition containing approximately 83% inert gas, 12% fuel gas and 5% oxidizer gas.

The introduction, at the point 22, of the oxidizer gas (the composition represented by the point C (air)) then causes the composition of the mixture to change from the point D to the point B along the line D-C.

It may be seen in this diagram that, in this case, both the initial and final compositions and the compositions of the mixture or of the intermediate mixture(s) during formation of the mixture remain outside the flammable region.

The solution which consists in firstly injecting the fuel gas at point 24 and then the oxidizer gas at the point 22 is therefore a completely safe solution. There is no flammability risk by proceeding in this manner.

Figure 4A:
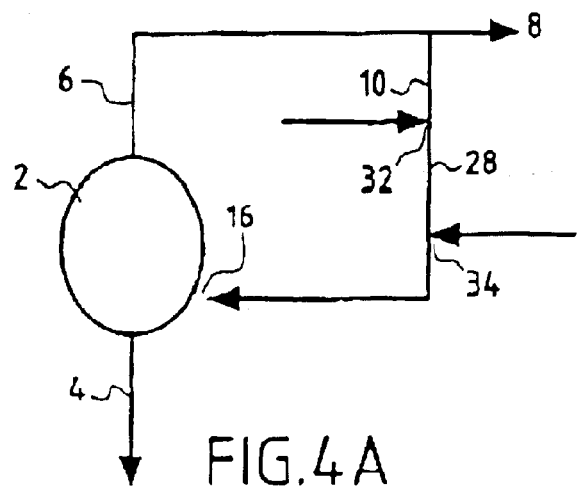

FIG. 4A represents a recycle scheme similar to the scheme in FIG. 2A. Identical numerical references denote similar or corresponding components. In this scheme, the oxidizer gas 32 is firstly injected into the recycle gas 10, in order to form a first, inert gas/oxidizer gas mixture 28. The fuel gas is then injected at the point 34, in order to form the final mixture injected into the reactor 2 at the point 16.

In the flammability diagram, this scheme firstly makes the composition pass from the point A to the point E (approximately 88% inert gas, 10% oxidizer and 2% fuel gas) and then to the point B, of composition already indicated above.

Initially, during its injection at the point 34, the fuel gas is pure (its composition is given by the point F at the vertex of the flammability diagram). To reach the point B, the mixture must therefore pass through the flammability region. This solution for mixing the gases therefore carries a flammability risk.

Figure 4B:
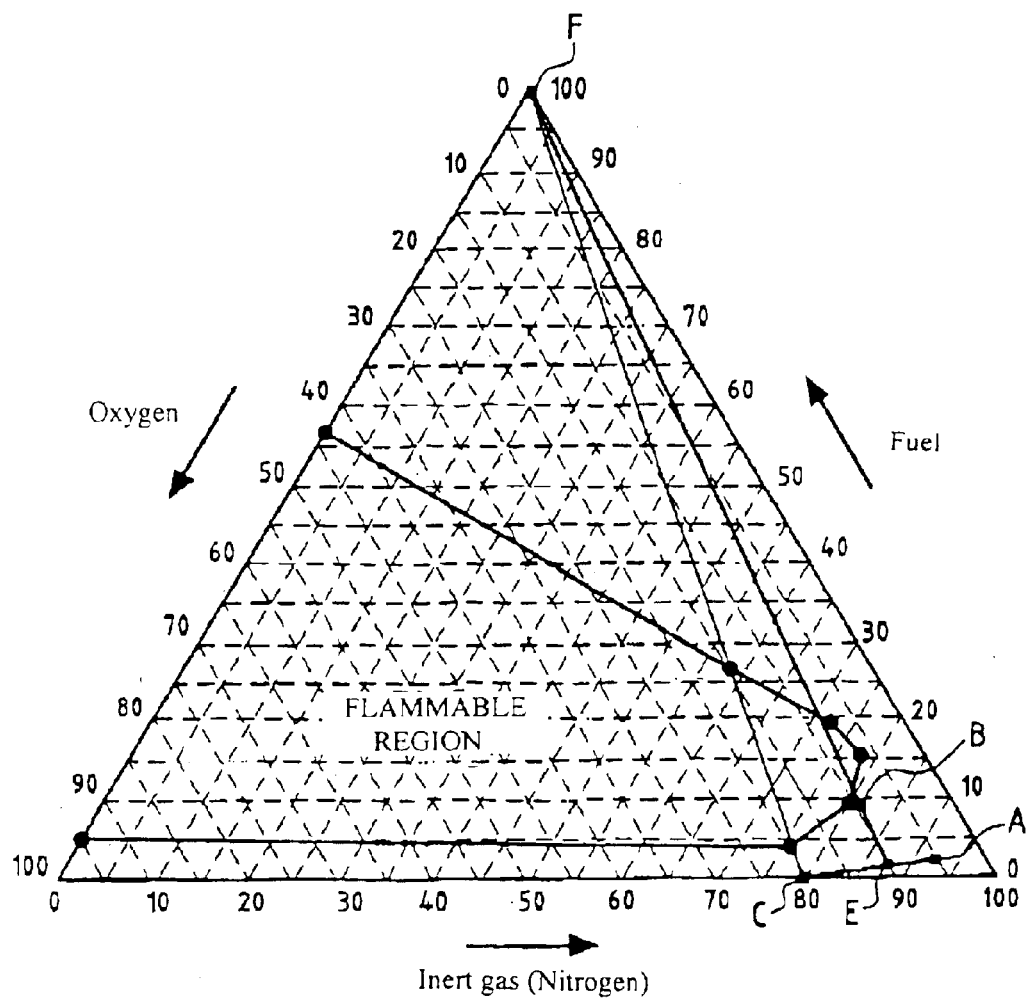

Comparing the two flammability diagrams in FIGS. 3B and 4B shows that it is the solution in FIG. 3A, which consists in firstly injecting the fuel in order to mix the latter with the recycle gas and then in injecting the oxidizer in order to form the final mixture, which is much safer than the second solution. It is therefore the first solution which must be adopted in order to form such a mixture. It is in the order prescribed by this first solution that the mixers will be placed, at the points 22 and 24 in FIG. 3A, in order to produce the plant.

Figure 5A:
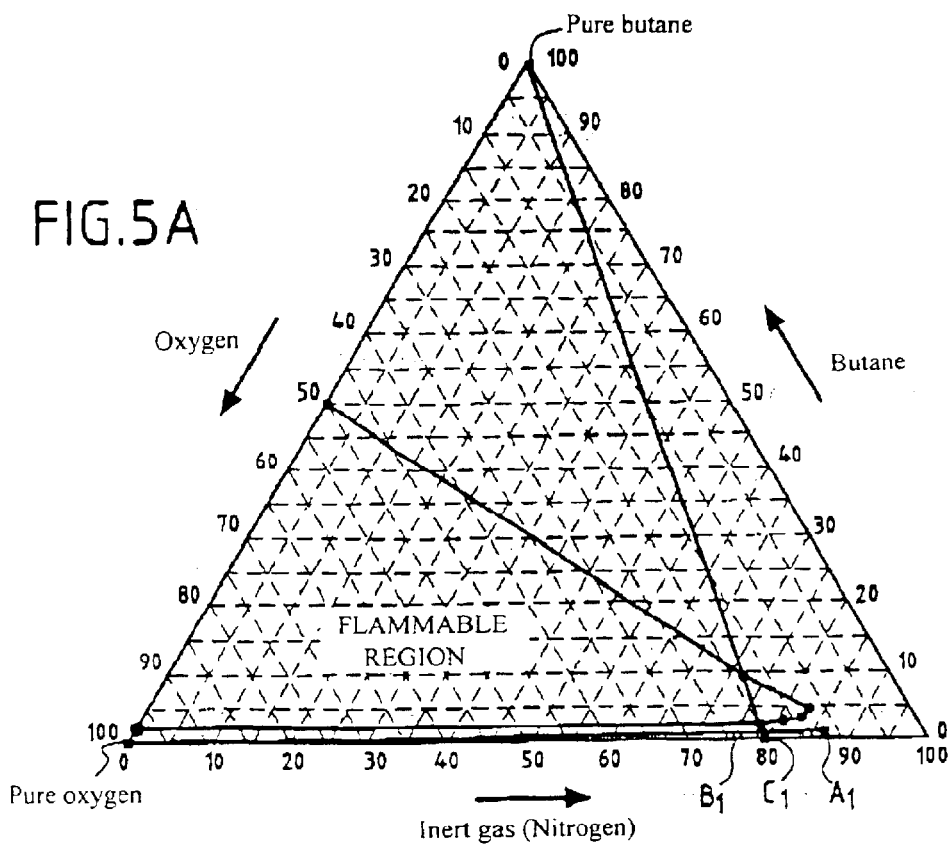
Figure 5B:
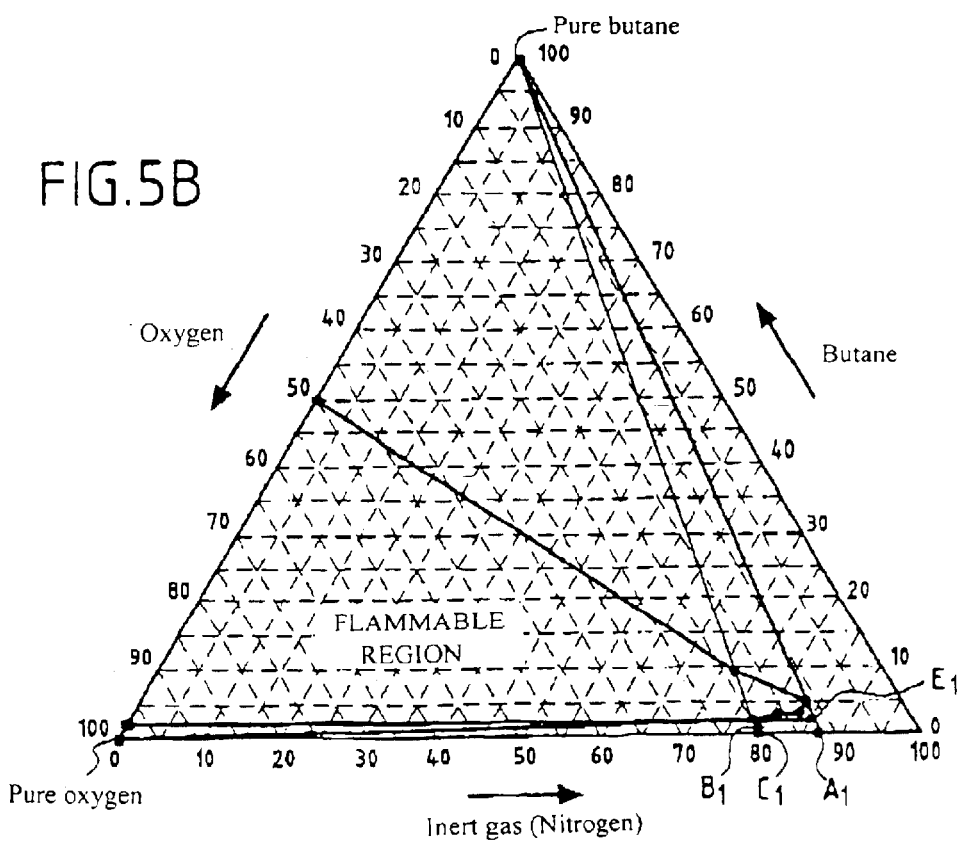

FIGS. 5A and 5B both represent flammability diagrams for the butane/oxygen/nitrogen ternary system. This is the ternary system encountered, for example, when carrying out the butane oxidation recycle process in the synthesis of maleic anhydride described, for example, in "Maleic anhydride", SRI International Report No. 46C, October 1989.

In FIG. 5A the recycle gas initially has the composition identified by the point $A_1$ (approximately 88% nitrogen and 12% oxygen).

On entering the reactor, the composition, dictated by the kinetics and by the operation of the reactor, is represented by the point $B_1$.

The recycle gas is firstly mixed with pure oxygen in order to obtain the composition identified by the point $C_1$. During formation of this first mixture, the gas composition therefore lies outside the flammable region and the mixture thus formed carries no flammability risk, even in the presence of an energy source.

The first mixture thus obtained is then mixed with pure butane until the desired composition $B_1$ is obtained. The injection of pure butane forces the composition to pass through the flammable region, as may be seen in the path in FIG. 5A, until the desired composition $B_1$ acquired at the inlet of the reactor is obtained.

On the other hand, in FIG. 5B, the recycle gas $A_1$ is firstly mixed with pure butane and then with oxygen. The composition of the mixture therefore passes from the point $A_1$ to the point $E_1$ in the flammability diagram (the line passing through $A_1$ and the vertex (pure butane) of the diagram does not intersect the flammability region) and then from the point $E_1$ to the point $B_1$, this time also without passing through the flammability region.

This second mixing scheme therefore has a much higher degree of safety than that in FIG. 5A. It corresponds to a recycle scheme of the type of that in FIG. 3A, in which the fuel (in this case, butane) is firstly injected or mixed, using an injector or a mixer, at the point 24 in order to form a mixture 18 of composition corresponding to the point $E_1$; the oxidizer is then injected or mixed, using an injector or a mixer, at the point 22 in order to form the mixture that has to be injected into or mixed in the reactor 2.

Figure 6A:
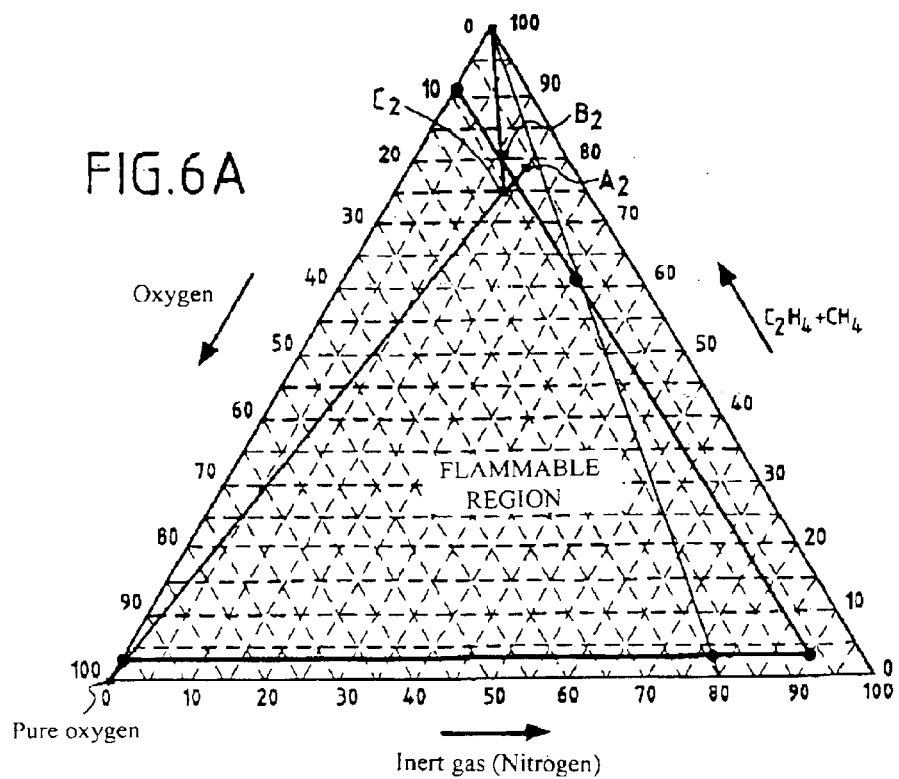
Figure 6B:
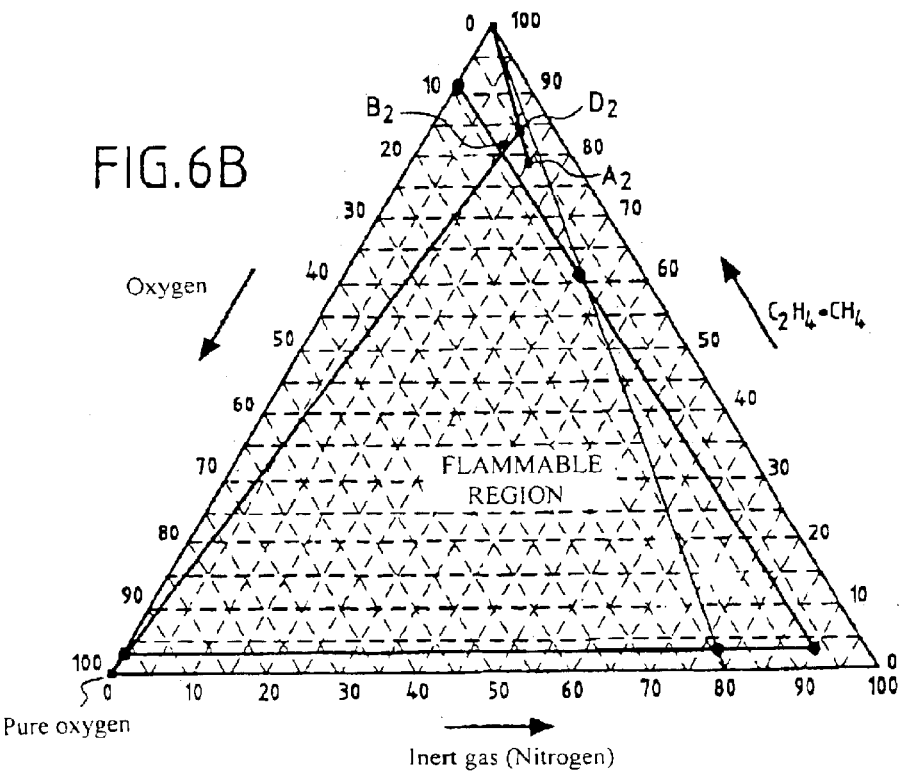

FIGS. 6A and 6B each represent the flammability diagram of the (ethylene+methane) /oxygen/nitrogen ternary system. This system is found when carrying out the ethylene oxidation recycle process in the synthesis of ethylene oxide, as described in "Ethylene oxide and ethylene glycol", SRI Consulting, Report No. 2F, January 1997.

In the scheme shown in FIG. 6A, the recycle gas (of initial composition $A_2$) is firstly mixed with pure oxygen. This mixing scheme is that in FIG. 4A. The first mixture 28 has a composition identified in the diagram by the point $C_2$ (approximately 13% inert gas, 13% oxygen and 74% fuel). This point $C_2$ lies within the flammable region. This means that, before the fuel (ethylene+methane) gas is injected, a first mixture carrying flammability risks is formed. It is only when forming the final mixture that the composition leaves the flammable region in order to reach the point $B_2$ (approximately 10% oxygen, 12% nitrogen and 78% fuel). This situation is very dangerous since the composition not only passes through the flammability region but it also forms an Intermediate mixture lying within this region. The flammability risk of this step, which results in the formation of this intermediate mixture, and therefore the risk of the entire injection mode, is very high.

In the diagram shown in FIG. 6B, which corresponds to the scheme in FIG. 3A, the recycle gas is firstly mixed with the ethylene/methane mixture in order to form a first mixture 18, to which oxygen is then added in order to form the second mixture injected into the reactor 2. In this case, the composition firstly changes from the point $A_2$ to the point $D_2$ (first mixture) without passing through the flammability region. During the oxygen injection, the composition passes well within the flammability region since it passes from pure oxygen to the point $B_2$ in the flammability diagram.

Nevertheless, this second solution is largely preferable to the first since it does not mean forming a mixture whose composition would lie within the flammable region.

What remains to be done is to compare the flammability time of the mixture with the transit time through the flammability region, or with the mixing time (which is greater than the transit time), in order to know whether or not the second solution is acceptable, however. At the temperature of the ethylene oxide synthesis process (160° C. at the inlet), this spontaneous ignition time being several minutes, the second solution is very acceptable since, as already explained, the mixing time is generally of the order of a few hundreds of milliseconds.

The system produced will therefore have the structure shown in FIG. 3A, the mixers being placed in the line 10 so as to firstly mix, at the point 24, the recycle gas with the ethylene/methane mixture in order to form a first mixture, to which oxygen is then added using a second mixer, located at the point 22, and thus form the final mixture.

Another illustrative example relates to the process for synthesizing hydrocyanic acid, described especially in document U.S. Pat. No. 5,882,618, which involves the oxidation of ammonia and of methane.

This process does not operate using a recycle gas. It is shown schematically in FIG. 7A. A $(CH_4+NH_3)$/air/oxygen mixture is firstly formed, by injecting methane, ammonia and oxygen into air at the point 42. The reactor 44 produces, on the one hand, gas HCN and, on the other hand, off-gases 46.

Figure 7A:
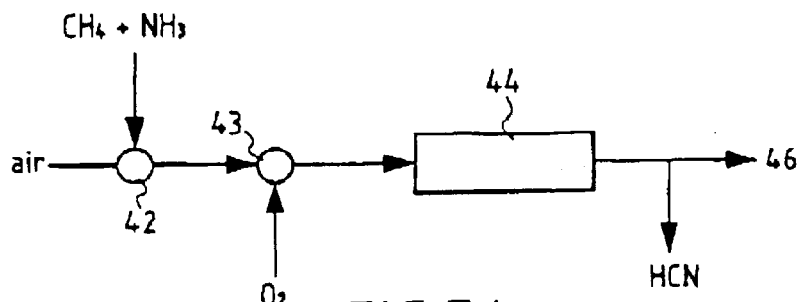
FIG. 7A shows another scheme for mixing gases.

Various injection modes may be defined:
  1st mode: injection of oxygen into air (first mixture) and then injection of $CH_4$ and $NH_3$ into this first mixture;
  2nd mode: injection of $CH_4$ and $NH_3$ into air (first mixture) and then injection of oxygen into this first mixture; it is this second mode that is shown in FIG. 7A;
  3rd mode: injection of $CH_4$ into air (first mixture), then injection of $NH_3$ into this first mixture (to form the second mixture) and finally injection of oxygen into this second mixture;
  4th mode: injection of $NH_3$ into air (first mixture), then injection of $CH_4$ into this first mixture (to form the second mixture) and finally injection of oxygen into this second mixture.

FIG. 7B shows the flammability regions corresponding to the ammonia/oxygen/inert gas mixture (curve I), to the methane/oxygen/inert gas mixture (curve II) and to a (52% methane+48% ammonia)/oxygen inert gas mixture (curve III). FIG. 7C shows only the flammability range of the (52% methane+48% ammonia)/oxygen/inert gas mixture. This region may, for example, be determined by using Le Chatelier's law, which makes it possible to plot the flammability regions using mixtures of fuels. Reference may be made on this subject to Kuchta, Bulletin 680, Bureau of Mines, 1985.

According to the first mode of injection, the oxygen may be firstly mixed with air in order to obtain the composition represented by the point $A_3$ (see FIG. 7). If a mixture consisting of 52% methane and 48% ammonia is then introduced, the composition will pass through the flammability region in order to reach the final composition of the operating point $B_3$.

If the mixture of fuels is firstly injected into air (first mixture) and then oxygen injected into the first mixture obtained (2nd mode), the composition passes through the flammability region twice. During formation of the second mixture (intermediate mixture with pure oxygen), the transit is long and the proportion of oxygen in the mixture may be high and therefore may make the mixture more reactive.

The first mixing method is therefore better.

This conclusion is confirmed by comparing the reactivity times of the mixture with the characteristic time of the mixer (which is greater than the transit time through the flammability region)—the first method has an acceptable risk whereas the second has a higher risk.

If the fuels are injected separately (3rd and 4th injection modes), the nitrogen/oxygen/1st injected fuel ternary diagram is firstly considered, in order to obtain a point representative of the composition of the second mixture, and then the nitrogen/oxygen/2nd injected fuel ternary diagram is considered, in order to obtain a point representative of the composition of the final mixture when starting from the composition of the second mixture.

In general, the treatment of the case in which at least three reactive gases or fuels are mixed with an inert or base gas therefore amounts to the successive treatment of several cases of mixing two gases with an inert or base gas.

It may thus be noted, given the position of the three injection points and of the composition of the final operating point (point $A_3$: 27% fuels (52% $CH_4$+48% $NH_3$), 17% oxygen and 56% nitrogen), that it is safer to firstly mix the air and oxygen and then to mix the fuels into this mixture. In this case, there is no advantage in injecting the fuels one after the other.

In order for the composition to pass through the flammability region only once, it is preferable to produce an air/oxygen and then a fuel mixture; in this case, it will be better to introduce a mixture of fuels, and to allow the composition to pass briefly through the tip of the flammability region, rather than to introduce the fuels one after another and to allow the composition to pass through "two tips" relating to the flammability regions of each of the fuels.

For the practical construction of the gas-mixing system, the points at which the oxygen and the $CH_4$+$NH_3$ mixture are injected are therefore the reverse of those in FIG. 7A. Placed at the point 42 is therefore a mixer for injecting oxygen and at the point 43 a mixer for adding the $CH_4$+$NH_3$ mixture to the first mixture thus formed.

Figure 9A:
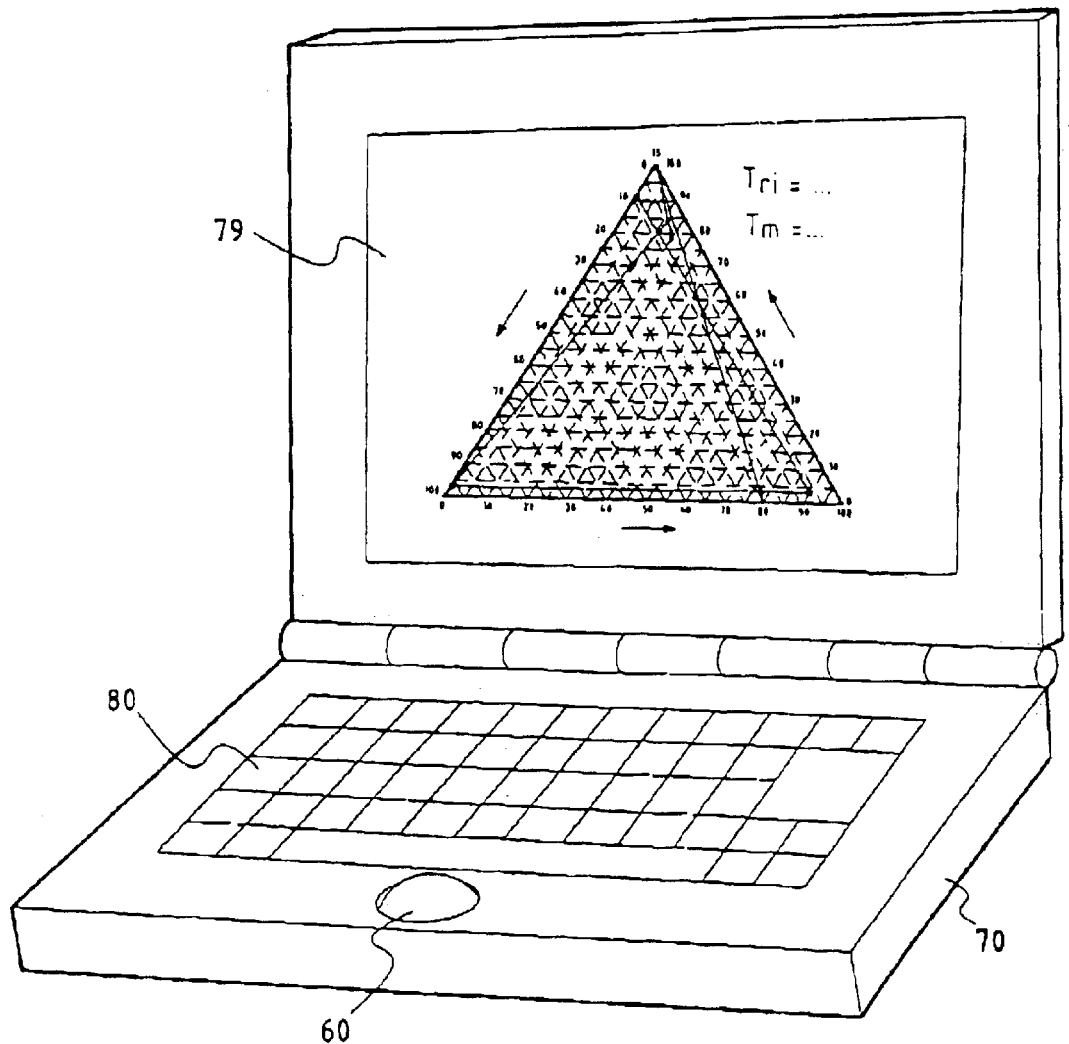
FIGS. 8 to 9B show an example of an apparatus for implementing the invention.

An illustrative example of a system allowing the implementation of the invention will be described in conjunction with FIGS. 8 to 9B.

Figure 8:
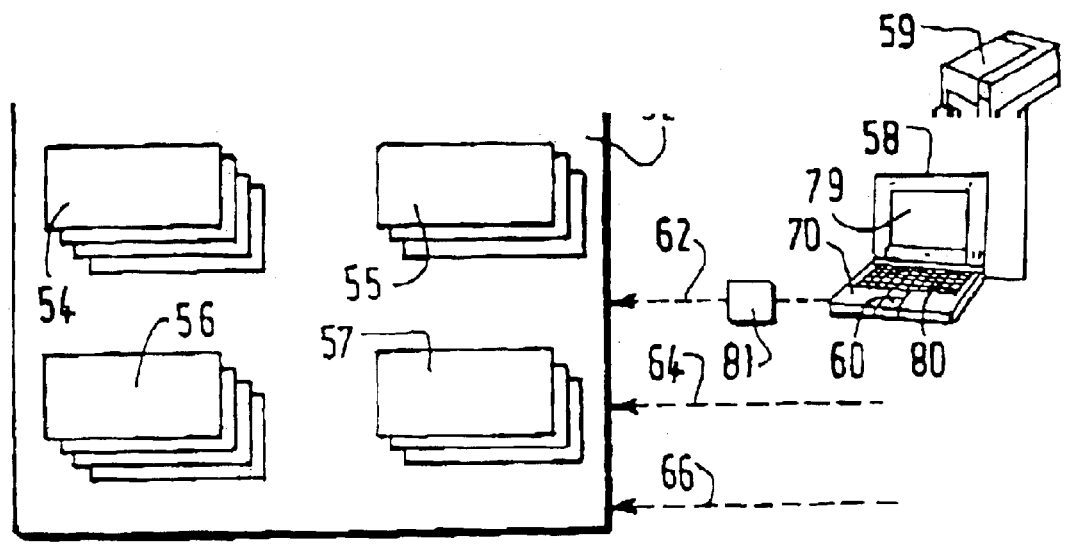
Figure 9B:
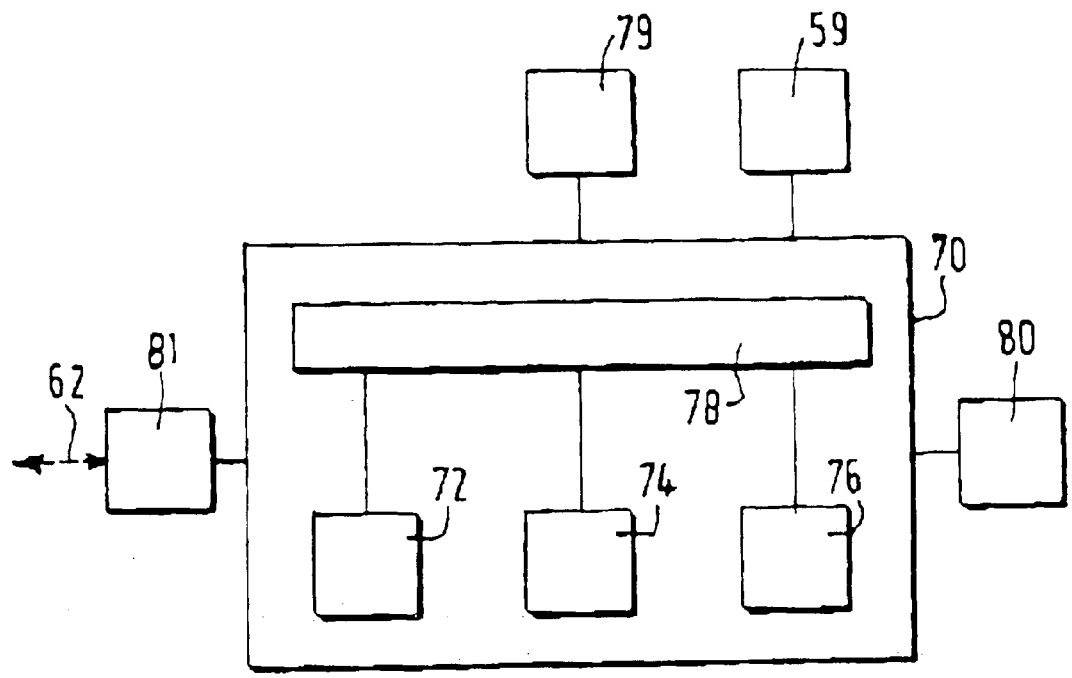

In FIG. 8, the reference 52 denotes either a central computer or a website. In the second case, this site is preferably accessible only via an intranet network.

In both cases, databases 54, 55, 56, 57 are stored in the computer or on the site. Such databases may be updated and relate respectively, for example to:

a database 54 in which fuel-gas ternary diagrams are recorded;
 a database 55 collecting, for various gases or gas mixtures, the induction times, or ignition times, and their change as a function of temperature and pressure data;
 a database 56 relating to various mixers, for example injectors, together with their mixing times; and
 optionally, a database 57 relating to the apparatus or equipment, for example pressure regulators and/or valves, etc., which can be used in combination with the injectors of the database 56 and the gases of the database 55.

Various users may be connected to the means 52 for storing these databases. In FIG. 8, one of these users is represented by his portable computer or PC-type computer 58, the connection with the means 52 being provided by a communication network 62, for example an intranet network 62, and by means of connection to this network (modem or network card 81).

Other users, not illustrated in the figure, may be connected, in parallel, to the storage means 52, via communication means 64, 66, etc., which may form part of a network. Each user's computer is also connected thereto by a modem or a network card.

According to a variant, the databases 54, 55, 56, 57 may also be stored in the storage means of the computing device 58, as long as the size of these databases and the memory size available in this computing system 58 are compatible.

The computing system 58 may, for example, be a commercial PC-type microcomputer. It is illustrated in FIG. 9A with a ternary diagram and a flammability region displayed.

It comprises (FIG. 9B) a central processing unit 70, which itself includes a microprocessor 72, a set 74 of ROM and RAM memories and a hard disk 76, which also has the function of storing information, all these components being coupled to a bus 78.

A screen 79 is used to display information on the data passed through into the system by an operator (for example, the name of a gas mixture and the temperature and pressure data for use of this gas mixture) and the data provided by the databases in response to the data input by the operator (for example, a ternary diagram and data on the chemical induction time of a mixture).

The system also has control peripherals and, in particular, a keyboard 80 and a mouse 60. Other means for selecting a region or a field of a page displayed on the screen 79 may also be used, for example any means allowing a selection to be made by tactile contact on the screen.

The instructions for implementing a procedure according to the invention are stored in the memory means 74, 76 of the computing system 58. The corresponding programs may also reside on a website 52 to which a user is connected via the terminal 58, the means 81 and the network 62.

According to another embodiment, all or some of the information contained in the databases 54, 55, 56, 57 is contained in the RAM memory of the computing system 58 and/or on the hard disk 76.

In response to the user's instructions, a connection is made between the system 58 and the means 52 which store the databases and, optionally, the programs to be used to run the procedure. These programs include, for example:

a program for determining the ignition times from the equations for the reaction kinetics;
 a program for determining the flammability regions, for example using Le Chatelier's law.;
 a program containing the instructions for carrying out a procedure as described above in conjunction with FIG. 1 (and therefore able to be organized according to the flow chart in FIG. 1) or according to one of its variants described above, and in particular allowing the transit time through one or more flammability regions or the mixing times and the chemical induction time(s) to be compared.

Here again, some of these programs may be contained in the memory of the computing system 58 and/or on the hard disk 76.

An interactive session may then be started, during which, in response to data input by the user, the system 52 sends this user data selected by searching in the databases 54, 55, 56, 57.

Using the computing system 58, a mixture is selected. The information specific to this mixture, and relating to its ternary diagram, with the corresponding flammability region for given temperature and pressure conditions, and optionally its induction time, are sought in the database 56 and sent to the computing system 58 and stored in the memory means 74, 76. This information or these data may also be computed from the abovementioned stored programs. They may be displayed on the screen 78. They may also be validated and corrected based on this display.

Then, a mixer (for example: an injector) is selected. The information specific to this mixer, and relating in particular to its mixing time, are sought in the database 56 (or possibly computed) and sent to the computing system 58 and then stored in the memory means 74, 76. This information may be displayed on the screen 78. It may also be validated and corrected.

All the data thus collected are stored in the memories 74, 76 of the computing system 58. They may also be sent to the central computer 52.

Data may also be input into the system 58, for example manually using the keyboard 80 and without recourse to a particular database. These data are also stored in the memories 74, 76 of the system 58, or sent to the system 52.

The ternary diagram and the various data on the induction and mixing times may be displayed on the screen 78.

The system 58 (or the means 52) may incorporate computing software for computing an induction time numerically, based on data provided by the user. It may also incorporate computing software for computing ternary diagrams and their flammability regions at various temperatures and/or pressures.

The instructions of the programs for carrying out a procedure according to the invention are stored in a memory region of the computing system 58 or of the system 52. These instructions are, for example, installed from a medium which can be read by the computing system 58 and on which they are recorded. Such a medium may, for example, be a hard disk, a read-only memory (ROM), a compact optical disk, a dynamic random-access memory (DRAM) or any other type of RAM memory, a magnetic or optical storage component, registers or other volatile and/or non-volatile memories.

What is claimed is:

1. A process for determining the risk of flammability of a mixture of at least two reactive gases A, B, in an inert or base gas, or the order of mixing of these reactive gases into the inert or base gas, the process comprising:
   a step of determining whether the composition of the mixture, during its formation, passes through a flammability region in a ternary diagram of the A/B/inert or base gas mixture when the mixture is produced according to a first mode in which A is first mixed into the inert or base gas to form a first mixture and then B is mixed into the first mixture to form the final mixture;
   a step of determining a first transit time through the flammability region of the ternary diagram when the mixture is produced according to the first mode;
   a step of comparing the first transit time with the chemical induction time of the mixture or of the stoichiometric mixture; and
   a step of determining the risk of flammability or the order of mixing based on a review of data received from the previously recited steps.

2. The process according to claim 1, further comprising a step of comparing one or more mixing times of a mixer or mixers used to prepare the mixture, with the chemical induction time of the mixture or of the stoichiometric mixture.

3. The process according to claim 1, further comprising:
   a step of determining whether the composition of the mixture passes through the flammability region of the ternary diagram, or whether the first transit time or the time of preparing the mixture is greater than the chemical induction time of the mixture; and
   a step of determining whether the composition of the mixture, during its formation, passes through the flammability region in the ternary diagram of the A/B/inert or base gas mixture, when the latter is produced according to a second mode in which B is first mixed into the inert or base gas to form a first mixture and then A is mixed into the first mixture to form the final mixture.

4. The process according to claim 3, further comprising:
   a step of determining a second transit time through the flammability region of the ternary diagram when the mixture is produced according to the second mode;
   a step of comparing the second transit time with the chemical induction time of the mixture or of the stoichiometric mixture.

5. The process according to claim 3, further comprising a step of comparing one or more mixing times of a mixer(s) used to prepare the mixture with the chemical induction time of the mixture or of the stoichiometric mixture.

6. The process according to claim 3, wherein, if the composition of one of the mixtures according to one of the modes of injection does not pass through the flammability region during its formation, this mode is selected.

7. The process according to claim 3, wherein a mode or the mode for which the time or times of preparing the mixture or the transit time through the flammability region of the ternary diagram is less than the chemical induction time of the mixture is selected.

8. The process according to claim 3, wherein, if the two modes of injection both force the composition to pass through the flammability region, selecting of the mode for which:
   (i) an intermediate mixture point, representative of the composition of the first mixture, lies outside the flammability region;
   (ii) the time or times of preparing the mixture or the transit time through the flammability region of the ternary diagram is less than the chemical induction time of the mixture.

9. A process for producing a mixture of at least two reactive gases A, B in an inert or base gas, comprising:
   determining the flammability risk of the mixture, while the mixture is being produced, or determining the order of mixing of the reactive gases into the inert or base gas, according to claim 1;
   mixing the reactive gases A and B in the order for which the composition of the mixture does not pass through the flammability region while the composition is changing, or for which the mixing time(s) or the transit time through the flammability region of the ternary diagram is (are) less than the chemical induction time of the mixture.

10. The process according to claim 1, further comprising a prior step of determining the mixing time or times of one or more mixers intended to be used for mixing reactive gases and for determining the temperature at which the spontaneous ignition time of the mixture becomes equal or substantially equal to one of the mixing times.

11. The process according to claim 1, wherein the mixing is carried out at a temperature of between 300° C. and 600° C.

12. The process according to claim 1, wherein the mixing of the two reactive gases A, B into an inert or base gas is that of a recycle process.

13. The process according to claim 1, wherein the mixture of the reactive gases is a mixture of oxygen and butane in an inert gas.

14. The process according to claim 1, wherein the mixture of the reactive gases is a mixture of oxygen and ethylene in an inert gas.

15. The process according to claim 1, wherein the reactive gases to be mixed into the inert or base gas are at least three in number and the order of mixing of the gases is determined by considering the pairs of gases that can be mixed successively, and the corresponding ternary diagrams.

16. The process according to claim 1, further comprising a step of consulting an electronic database containing data on ternary diagrams and/or consulting an electronic database containing data on induction times of gas mixtures and/or consulting an electronic database containing data on mixing times of mixers.

17. The process according to claim 1, further comprising a graphical representation on a display screen, of the ternary diagram(s) in question and of the corresponding flammability region(s) in this diagram(s).

18. A process for producing a plant for mixing at least two reactive gases A, B into a base gas, comprising:

determining the order of mixing the gases according to claim 1; and producing a plant so as to mix the gases in the order thus determined.

19. A computer program comprising the instructions for executing a process according to claim 1.

20. A data medium, which can be read by a computing system, comprising the data, in coded form, for executing a process according to claim 1.

* * * * *